United States Patent
Gim

(10) Patent No.: US 8,968,170 B2
(45) Date of Patent: Mar. 3, 2015

(54) INTRAUTERINE RADIATION DEVICE AND SYSTEM COMPRISING AN INDIVIDUALLY INFLATING BALLOON

(75) Inventor: Chang Uk Gim, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 247 days.

(21) Appl. No.: 13/496,853

(22) PCT Filed: Sep. 20, 2010

(86) PCT No.: PCT/KR2010/006490
§ 371 (c)(1),
(2), (4) Date: May 8, 2012

(87) PCT Pub. No.: WO2011/034403
PCT Pub. Date: Mar. 24, 2011

(65) Prior Publication Data
US 2012/0215053 A1      Aug. 23, 2012

(30) Foreign Application Priority Data

Sep. 21, 2009  (KR) .................. 10-2009-0089277
Sep. 20, 2010  (KR) .................. 10-2010-0092496

(51) Int. Cl.
| A61N 5/00 | (2006.01) |
| A61M 36/00 | (2006.01) |
| A61M 36/10 | (2006.01) |
| A61N 5/10 | (2006.01) |
| A61B 18/00 | (2006.01) |

(52) U.S. Cl.
CPC ..... *A61N 5/1016* (2013.01); *A61B 2018/00577* (2013.01)
USPC ............................................. 600/6

(58) Field of Classification Search
CPC . A61N 5/1001; A61N 5/1015; A61N 5/1016; A61F 13/26
USPC ......................................... 600/6; 604/11, 14
See application file for complete search history.

(56) References Cited

U.S. PATENT DOCUMENTS

| 3,872,856 | A | * | 3/1975 | Clayton .......................... 600/6 |
| 5,623,932 | A |   | 4/1997 | Ramanujam et al. .......... 128/665 |
| 5,720,717 | A | * | 2/1998 | D'Andrea ........................ 604/21 |
| 2006/0043314 | A1 | * | 3/2006 | Katzir et al. .................. 250/484.5 |
| 2009/0018383 | A1 | * | 1/2009 | Corcione et al. ................. 600/7 |
| 2010/0010287 | A1 | * | 1/2010 | Lubock ........................... 600/7 |

FOREIGN PATENT DOCUMENTS

| JP | 08-511179 | 11/1996 |
| KR | 10-2005-0074013 | 7/2005 |

* cited by examiner

*Primary Examiner* — Jacqueline Cheng
*Assistant Examiner* — Kaylee Wilson
(74) *Attorney, Agent, or Firm* — Hammer & Associates, P.C.

(57) ABSTRACT

Provided is an intrauterine radiation device and system having individually inflating balloons, which constantly expand the inside of the vagina to a desired degree using the balloons in accordance with treatment planning during uterine brachytherapy, which enable the position of a radiation applicator to be accurately reproduced, and which apply a precise dose of radiation determined according to the treatment planning.

20 Claims, 4 Drawing Sheets

INTRAUTERINE RADIATION DEVICE AND SYSTEM COMPRISING AN INDIVIDUALLY INFLATING BALLOON

CROSS-REFERENCE TO RELATED APPLICATION

This application claims priority to and the benefit of Korean Patent Application No. 2009-0040218, filed May 8, 2009, the disclosure of which is incorporated herein by reference in its entirety.

BACKGROUND

1. Field of the Invention

The present invention relates to an intrauterine radiation device and system, and more particularly, to an intrauterine radiation device and system having individually inflatable balloons, which constantly expand the inside of the vagina to a desired degree using the balloons in accordance with treatment planning during uterine brachytherapy, which enable the position of a radiation applicator to be accurately reproduced, and which apply a precise dose of radiation determined according to the treatment planning.

2. Discussion of Related Art

In general, to treat a patient for a disease occurring in the uterus such as uterine cancer, brachytherapy is performed on the uterus by applying radiation to a diseased part of the uterus. To apply the radiation, radiation source mobile instruments are used. The radiation source mobile instruments are devices that move a radiation source, and generally include a tandem and an ovoid.

When the treatment is performed using the radiation source mobile instruments, the vagina is first expanded using a speculum. In this state, an operator inserts an intrauterine insertion instrument called a tandem into the uterus while directly looking at the tandem.

Subsequently, the speculum is removed from the vagina, and then an intravaginal insertion instrument called an ovoid is pushed into the vagina. In this case, since the operator does not look at a depth of insertion of the ovoid, the operator intuitively pushes the ovoid into the vagina. Here, the speculum is removed in order to insert the ovoid into the vagina to prevent the ovoid from being caught by the speculum due to a size of the ovoid when the ovoid is inserted.

To immobilize the radiation source mobile instruments, i.e. the tandem and the ovoid, which have been inserted in this way, and to prevent unnecessary radiation from being applied to organs such as the bladder and the rectum adjacent to the vagina, the operator directly inserts and packs gauze into the vagina and the uterus.

Such radiation source mobile instruments have the following problems.

First, the gauze is packed around the tandem and the ovoid. An amount, a thickness, an insertion depth, an insertion direction, etc. of the gauze are difficult to equally reproduce whenever the treatment is performed. If the radiation source mobile instrument packed with the gauze is changed in position whenever the treatment is performed, it is difficult to perform an accurate operation.

Second, the number of radiation source mobile instruments used is generally three. Thus, it is difficult to obtain more diverse, selective distributions of the radiation dose.

Third, when radiating from the radiation source, the radiation generally has a characteristic of being constantly emitted from the same center toward its surroundings. Thus, if a position of a tumor is biased in one direction or the tumor has an irregular shape, the radiation source mobile instrument does not apply the radiation only to the tumor, but to the surrounding normal organs. As a result, the radiation source mobile instrument may actually have an adverse effect on the normal organs.

SUMMARY OF THE INVENTION

The present invention is directed to providing an intrauterine radiation instrument and system having individually inflatable balloons, which allow radiation to be applied only to a specific tumor so as to reduce an adverse effect on normal organs.

The present invention is also directed to providing an intrauterine radiation instrument and system having individually inflatable balloons, which allow radiation source mobile instruments to be accurately located at desired positions whenever treatment is performed.

The present invention is also directed to providing an intrauterine radiation instrument and system having individually inflatable balloons, which are capable of obtaining diverse distributions of a dose of radiation.

The present invention is also directed to providing an intrauterine radiation instrument and system having individually inflatable balloons, which are capable of measuring a dose of radiation.

An aspect of the present invention provides an intrauterine radiation device having individually inflatable balloons, which includes: a hollow cylindrical cylinder in which a plurality of air tubes are installed and into which radiation source mobile instruments are inserted; and a plurality of front balloons that are mounted on an outer circumferential surface of a front end of the cylinder in a direction in which the cylinder is inserted, and that are connected with the air tubes so as to be individually inflated.

Here, the intrauterine radiation device may further include a middle balloon that is spaced apart from the front balloons, mounted on the outer circumferential surface of the cylinder, and connected with the air tube so as to be inflated.

Further, the front end of the cylinder may be bent in a radially inward direction, and the front balloons may be mounted on an outer surface of the front end, and simultaneously inflated in thickness and insertion directions of the cylinder.

Also, the front end of the cylinder may be partitioned into a plurality of split sleeves, and the front balloons may be mounted on the split sleeves, and simultaneously inflated in thickness and insertion directions of the cylinder.

Further, the split sleeves may be hinged with the cylinder, and formed to be bent at front ends thereof in a radially inward direction.

Meanwhile, the intrauterine radiation device may further include at least one holder that is formed on an inner circumferential surface of the cylinder.

Further, the holder may protrude from the inner circumferential surface of the cylinder in a radially inward direction and have a semi-circular cross section.

Also, the holder may be recessed from the inner circumferential surface of the cylinder.

In addition, after the radiation source mobile instrument is mounted on the holder, a shield may be mounted around the radiation source mobile instrument so as to shield the radiation.

As described above, when uterine brachytherapy is performed with the intrauterine radiation instrument or system having individually inflatable balloons according to the present invention, the inside of the vagina can be constantly expanded to a desired degree in a desired direction, and the positions of the radiation source mobile instruments, each of which moves a radiation source, can be accurately reproduced. Further, an accurate dose of radiation determined according to treatment planning can be applied.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

An intrauterine radiation device having individually inflatable balloons according to an exemplary embodiment of the present invention will be described below in detail with reference to the appended drawings.

The appended drawings show illustrative forms of the invention, and are merely provided to describe the invention in greater detail. Thus, the technical scope of the invention is not limited to the drawings.

Figure 1:
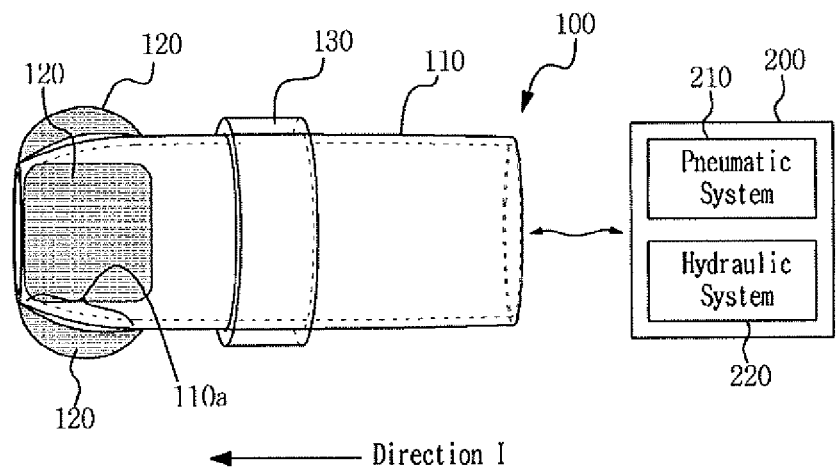
FIG. 1 is a conceptual view showing an auxiliary instrument for uterine brachytherapy according to an exemplary embodiment of the present invention.

FIG. 1 is conceptual view showing an intrauterine radiation device having individually inflatable balloons according to an exemplary embodiment of the present invention.

Figure 2:
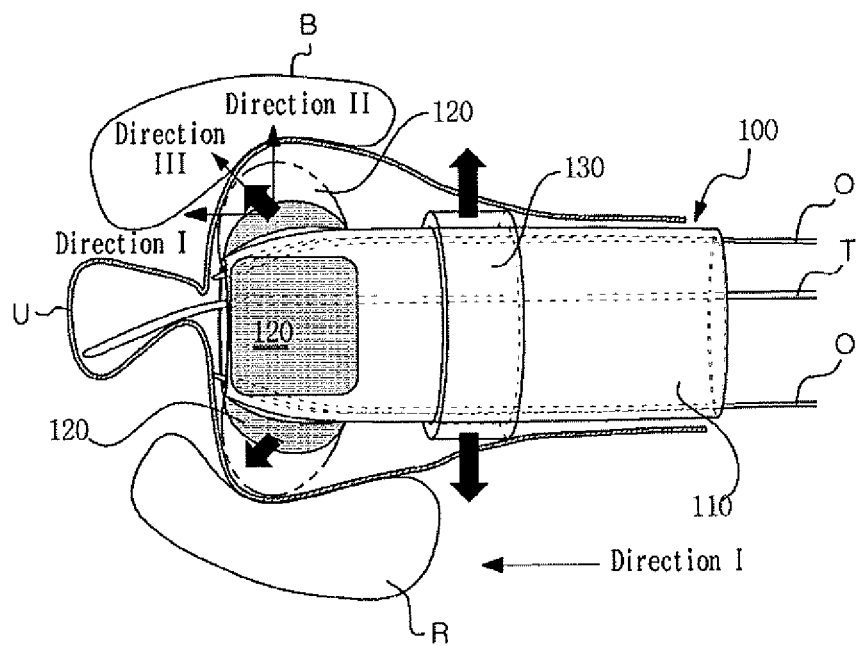
FIG. 2 is a conceptual view showing a state in which the auxiliary instrument for uterine brachytherapy shown in FIG. 1 is located inside a vagina.
Figure 7:
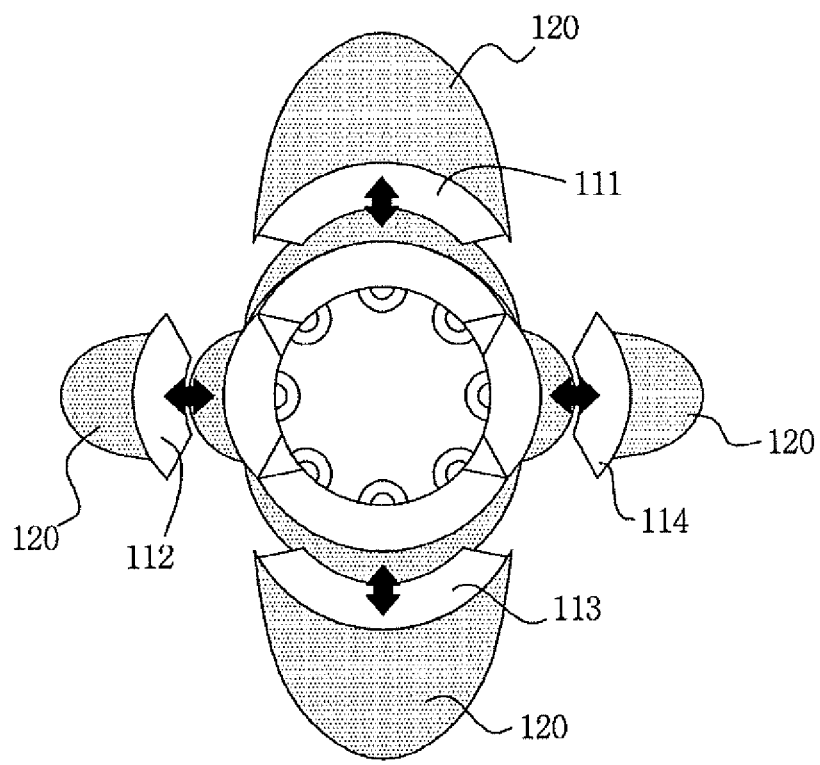
FIGS. 7 and 8 are partial cross-sectional views showing an operation of an auxiliary instrument for uterine brachytherapy according to another exemplary embodiment of the present invention.
Figure 8:
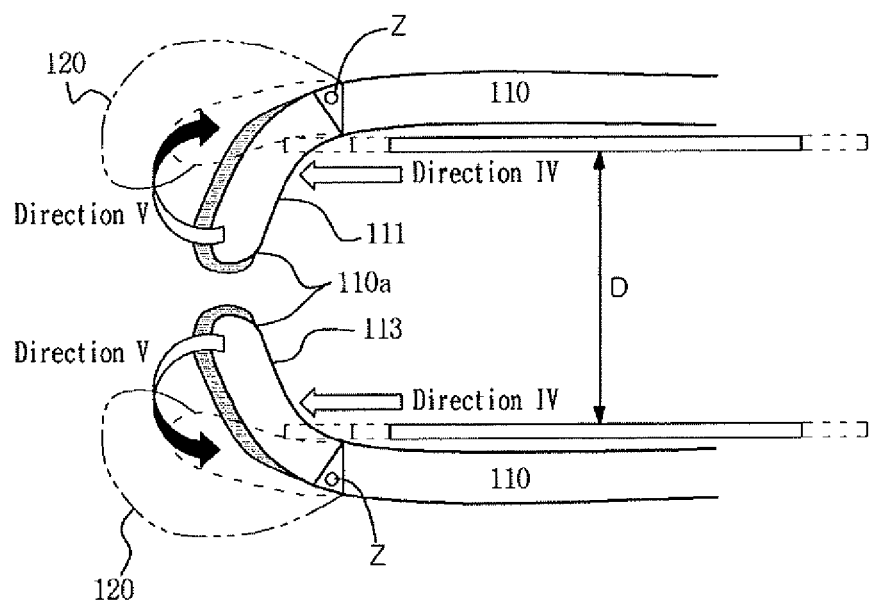

FIG. 2 is a conceptual view showing a state in which the intrauterine radiation device shown in FIG. 1 is located inside a vagina. FIGS. 3, 4, 5 and 6 are partial cross-sectional views showing an operation of the intrauterine radiation device according to the exemplary embodiment of the present invention. FIGS. 7 and 8 are partial cross-sectional views showing an operation of an intrauterine radiation device according to another exemplary embodiment of the present invention.

Embodiment 1

Figure 3:
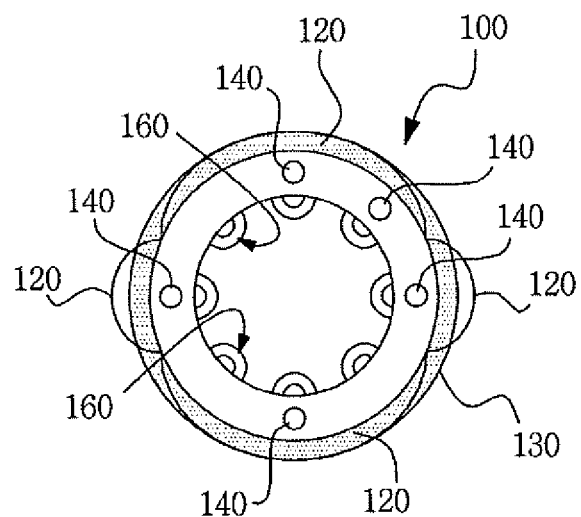
FIGS. 3 to 6 are partial cross-sectional views showing an operation of the auxiliary instrument for uterine brachytherapy according to the exemplary embodiment of the present invention.

The intrauterine radiation device 100 having individually inflatable balloons according to the exemplary embodiment of the present invention includes a hollow cylindrical cylinder 110, and front balloons 120 mounted on the cylinder 110 (see FIGS. 1 to 3).

The cylinder 110 is equipped therein with a plurality of air tubes 140, and radiation source mobile instruments O and T (see FIG. 2).

The front balloons 120 are radially mounted on an outer circumferential surface of a front end of the cylinder 110 in a direction in which the cylinder 110 is inserted (direction I, see FIGS. 1 and 2), and are connected with the air tubes 140 so as to be individually inflated.

The front balloons 120 may be inflated by external injection means 200. The injection means 200 injects air or water through the air tubes 140, and may include a pneumatic system 210 or a hydraulic system 220.

Here, the front balloons 120 are mounted in a mutually separated pattern, and are individually inflated by injection of air from the air tubes 140.

As shown in FIG. 3, the front balloons 120 may be disposed on upper, lower, left and right sides, i.e. a total of four sides, of the front end of the cylinder 110.

Here, the front balloons 120 may be connected to the air tubes 140, respectively. Otherwise, a pair of left and right or upper and lower front balloons may be connected to one air tube. Here, the number of front balloons 120 and the number of air tubes 140 may be changed. For example, as shown in FIG. 3, five air tubes 140 may be provided to inject air to four front balloons 120 and one middle balloon 130 to be described below.

Meanwhile, as shown in FIG. 1, the front end 110a of the cylinder 110 is bent toward the inside (an inward direction of the cylinder). The front balloons 120 can be mounted on an outer surface of the front end 110a.

Thereby, the front balloons 120 can be inflated in a thickness direction (direction II) or an inserting direction (direction I) of the cylinder 110, or in the two directions at the same time, i.e. in a resultant direction (direction III).

Meanwhile, as shown in FIGS. 1 and 2, the intrauterine radiation device 100 may further include a middle balloon 130 that is spaced apart from the front balloons 120, mounted on the outer circumferential surface of the cylinder 110, and connected with the air tube 140 so as to be inflated.

The middle balloon 130 is inflated on a mouth side of the vagina, thereby preventing the intrauterine radiation device 100 of the present invention from being pushed out of the vagina and securing the mouth of the vagina.

Meanwhile, the front balloons 120 and the middle balloon 130 can be inflated or contracted by injecting or discharging external air or water, and may be formed of one of resins having excellent inflatability without restriction, for instance, a polyvinyl resin.

An operation of the intrauterine radiation device 100 as described above will be described with reference to FIG. 2.

First, the intrauterine radiation device 100 is inserted into the vagina. Then, the front balloons 120 are located at an inner end of the vagina, and are individually inflated to push normal organs B and R. Here, B indicates the bladder, and R indicates the rectum.

Particularly, a plurality of front balloons 120 (e.g. four front balloons 120 in this embodiment) are provided in a circumferential direction of the cylinder 110, and are connected with a plurality of air tubes 140 so that the front balloons 120 can be inflated so as to have different volumes. Thereby, the present invention has an advantage in that the intrauterine radiation device 100 can be immobilized by adjusting a degree of inflation of each front balloon 120 to expand the inside of the vagina in a desired shape.

The present invention resolves a conventional problem that, since gauze is packed around each radiation source mobile instrument and since the packed gauze varies in an amount or an angle, radiation cannot be applied to a previously set accurate position when a future operation is performed. That is, the present invention has an advantage in that, since an amount of air or water injected into each front balloon 120 can be checked, only such an amount is injected when a future operation is performed, so that the future operation can be performed by disposing the radiation source mobile instruments O and T at positions at which the previous operation was performed. A degree of injection of air for expanding the vagina can be checked using a gauge, and is recorded so as to secure reproducibility of the expansion.

Further, the present invention can minimize conventional geometrical errors of a tandem T (see FIG. 2) or an ovoid O (see FIG. 2), the errors of which may occur during treatment due to the packed gauze, and reduce a treatment preparing time and discomfort of a patient because the packed gauze can be omitted if necessary.

In addition, since the front balloons 120 can be independently inflated or contracted, the normal organs B and R (see FIG. 2) move away in predetermined directions (e.g. in upward and downward directions), so that an unnecessary dose of radiation can be prevented from being applied to the normal organs. Here, the front balloons are inflated to such a degree that a patient does not suffer pain in the other directions (e.g. in leftward and rightward directions), so that more comfortable treatment can be provided to the patient. For example, if the front balloons are excessively inflated in the upward and downward directions, normal endovaginal tissues become narrow, and thus an unnecessary dose of radiation may be applied to these tissues. As such, it is necessary to somewhat inflate the front balloons in the leftward and rightward directions.

To this end, the front balloons 120 bring the air tubes 140 into a relation of one-to-one correspondence, so that they can be filled with fluid such as air or water.

Meanwhile, the number of front balloons 120 is not substantially restricted. As described above, the four front balloons may be symmetrical with respect to the central line of the cylinder 110.

Figure 4:
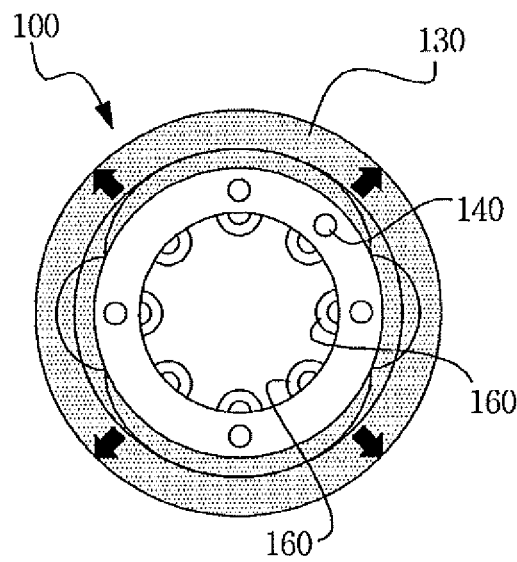

The intrauterine radiation device 100 may further include at least one holder 160 formed on an inner circumference surface of the cylinder 110 at intervals (see FIGS. 3 and 4).

Figure 5:
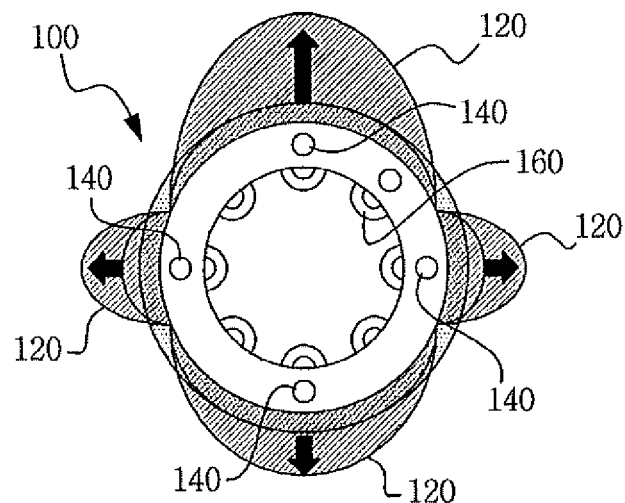

The tandem T (see FIG. 2) or the ovoid O (see FIG. 2) may be mounted in the holder 160. As shown in FIGS. 3 to 5, the holder 160 is formed so as to protrude from the inner circumference surface of the cylinder 110 in a radially inward direction in a semi-circular cross-sectional shape (hereinafter referred to as "convex holder").

Figure 6:
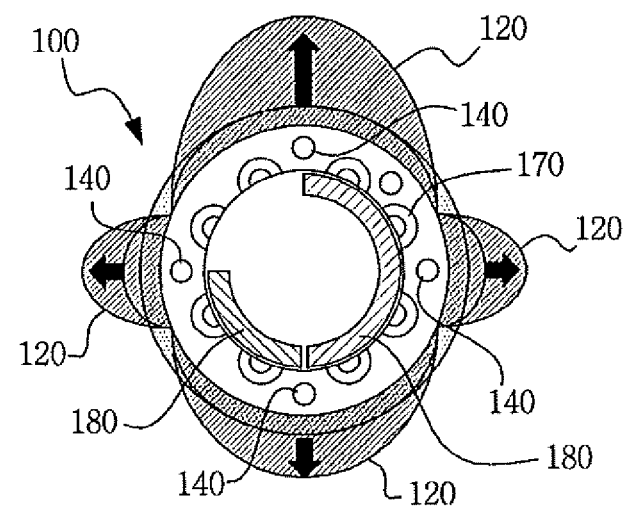

As shown in FIG. 6, the holder may be formed so as to protrude from the inner circumference surface of the cylinder 110 in a radially outward direction (hereinafter referred to as "concave holder 170").

A plurality of convex or concave holders 160 or 170 may be formed to additionally mount the radiation source mobile instruments.

As described above, the three radiation source mobile instruments, i.e. a pair of ovoids O (see FIG. 2) and one tandem T (see FIG. 2), are used in the related art. As such, it is difficult to obtain various and selective distribution of the dose of radiation. However, the present invention has an advantage in that it can obtain more various and selective distribution of the dose of radiation than the related art by installing the additional ovoids on the plurality of holders 160 or 170 or mounting them at various positions.

Meanwhile, when the concave holders 170 are formed as shown in FIG. 6, the radiation source mobile instruments may be mounted in the holders 170, and then a shield 180 may be mounted around the radiation source mobile instruments. Radiation is applied in a specific direction by the shield 180, so that the normal organs can be protected. The shield 180 may be inserted into the cylinder 110 as a semi-circular shield 181 or as a quadrant shield 182. The shield 180 may be formed of lead (Pb). A shape of the shield 180 may be dependent on the number of radiation source mobile instruments or a shape of the radiation source mobile instrument. As the material of the shield 180, any material that is able to shield the radiation may be used.

A thermoluminescence dosimeter (TLD) may be installed in the cylinder 110 or the front balloon 120 so as to be able to measure an actual dose of radiation applied to a desired position. Thus, a dose of radiation planned by a computer is compared with an absolute dose of radiation, so that accurate treatment can be performed. When exposed to radiation, the TLD contains the radiation, and releases a dose of radiation when heated. Thus, an actual dose of radiation can be measured at a desired position by the TLD, and an accurate operation can be performed in future treatment.

Meanwhile, the front end 110a of the cylinder 110 is partitioned into a plurality of split sleeves, and the front balloons 120 may be mounted on the split sleeves. As shown in FIG. 7, four split sleeves 111, 112, 113 and 114 are formed, and the four front balloons 120 may be mounted on the four split sleeves 111, 112, 113 and 114, respectively. The number of split sleeves and the number of front balloons may vary.

As described above, the front balloons 120 can be inflated in the thickness direction (direction II, see FIG. 2) or the inserting direction (direction I, see FIG. 2) of the cylinder 110, or in the two directions at the same time.

As shown in FIG. 8, the front end 110a of the split sleeves 111, 112, 113 and 114 may be bent in a radially inward direction as described above. Since the front end 110a has elasticity, the front end 110a can be deformed in a radially outward direction of the cylinder 110, and then be restored to an original shape by the elasticity.

Since a diameter of the uterus is greater than that of the vagina, the organs around the front balloons may not be easily pushed only by the inflation of the front balloons 120. As such, as shown in FIG. 8, the split sleeves 111, 112, 113 and 114 are pushed in the inserting direction (direction IV) of the cylinder 110, and thus are rotated in an outward direction (direction V) of the cylinder 110. Then, the front balloons 120 are inflated to be able to push the surrounding organs.

Meanwhile, the split sleeves 111, 112, 113 and 114 may have elasticity so as to be able to return to their original positions after being rotated in the direction V. Further, the split sleeves 111, 112, 113 and 114 may be coupled with the cylinder 110 using respective hinges Z so as to be able to be rotated in the direction V. The front end 110 a of the split sleeves 111, 112, 113 and 114 may also be bent in a radially inward direction. Here, the hinge Z is a device that allows one member to be pivoted relative to another member. This hinge is well known, and thus is conceptually shown in FIG. 8.

As shown in FIG. 8, the split sleeves 111, 112, 113 and 114 may be rotated in a radially outward direction of the cylinder 110, i.e. in the direction V, by pushing push rods D in the direction IV.

Embodiment 2

In this embodiment, a method S100 of applying intrauterine radiation using the intrauterine radiation device 100 described in Embodiment 1 will be described.

First, after the intrauterine radiation device 100 is inserted into the vagina, the front balloons are inflated to immobilize the radiation source mobile instruments at desired positions. Then, an operation is performed. Here, a rate of flow required to inflate the front balloons is checked (S110).

Since the front balloons of the present invention are individually inflated, the surrounding organs can be pushed by desired distances, and thus the radiation source mobile instruments can be disposed at desired positions. This is as described above.

Meanwhile, it is necessary to check the positions of the surrounding organs. Anatomical positions of the organs can be checked by injecting a contrast medium into the organs and x-raying the organs.

Information about the flow rate for inflating the front balloons is obtained in step S110, and the subsequent step S120 is performed.

Step S120 is applied to an additional operation after a first operation has been performed. After the intrauterine radiation device 100 is inserted into the vagina, the checked flow rate is injected into the front balloons, and thus the radiation source mobile instruments are disposed at positions at which the first operation was performed. Then, the radiation is applied to perform the additional operation.

That is, the information about the flow rate for inflating the front balloons is first obtained by this method S100. Then, the front balloons are inflated based on the obtained information about the flow rate when the future operation is performed. Thereby, the conditions in which the first operation was performed can be accurately reproduced.

In this manner, since the present invention can obtain predetermined information about the flow rate after the first operation has been performed, and the obtained conditions of the first operation can be accurately reproduced when the future operation is performed, it resolves the conventional problem occurring when the radiation source mobile instruments are packed using the gauze (i.e. the problem that the positions of the radiation source mobile instruments when the first operation is performed are changed by repetition of the operation because an amount, an angle, etc. of packed gauze vary whenever the operation is performed).

Embodiment 3

In this embodiment, a method S200 of applying intrauterine radiation will be described as in Embodiment 2.

In detail, the method S200 includes inserting the intrauterine radiation device 100 into the vagina, inflating the front balloons in such a manner that the balloon adjacent to a diseased part is less inflated than the other balloons, and concentrating the radiation radiating from the radiation source mobile instruments on a diseased part.

The method S200 of the present invention allows a distance between the diseased part and the radiation source mobile instrument to be reduced to focus the radiation on the diseased part.

Further, since the balloons adjacent to the normal organs are relatively more inflated, a distance between the normal organs and the radiation source mobile instrument is increased, so that a dose of the radiation applied to the normal organs can be remarkably reduced.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An intrauterine radiation device having individually inflatable balloons, comprising:
   a hollow cylindrical cylinder in which a plurality of air tubes are installed and into which radiation source mobile instruments are inserted and through which the radiation source mobile instruments pass;
   at least one holder having at least one convex or concave shape, that is formed on an inner circumferential surface of the cylinder and configured to hold the radiation source mobile instruments; and
   a plurality of front balloons that are mounted on an outer circumferential surface of a front end of the cylinder in a direction in which the cylinder is inserted, and that are connected with the air tubes so as to be individually inflated,
   wherein the front end of the cylinder is partitioned into at least four split sleeves along a circumferential direction of the cylinder, and each front balloon is mounted on each split sleeve, and is allowed to be simultaneously inflated in thickness and insertion directions of the cylinder.

2. The intrauterine radiation device of claim 1, further comprising a middle balloon that is spaced apart from the front balloons, mounted on the outer circumferential surface of the cylinder, and connected with one of the plurality of air tubes so as to be inflated.

3. The intrauterine radiation device of claim 1, wherein the front end of the cylinder is bent in a radially inward direction.

4. The intrauterine radiation device of claim 1, wherein the front balloons are inflatably mounted so as to have different volumes.

5. The intrauterine radiation device of claim 1, wherein the front balloons bring the air tubes into a relation of one-to-one correspondence.

6. The intrauterine radiation device of claim 1, further comprising a thermoluminescence dosimeter that is installed in the cylinder or the front balloon so as to measure a dose of radiation.

7. The intrauterine radiation device of claim 1, wherein the holder is a convex holder that protrudes from the inner circumferential surface of the cylinder in a radially inward direction and has a semi-circular cross section.

8. The intrauterine radiation device of claim 1, wherein the holder is a concave holder that is recessed from the inner circumferential surface of the cylinder.

9. The intrauterine radiation device of claim 8, wherein, after the radiation source mobile instrument is mounted on the holder, a shield is mounted around the radiation source mobile instrument so as to shield the radiation.

10. The intrauterine radiation device of claim 1, wherein the split sleeves are bent at front ends thereof in a radially inward direction so as to have elasticity, and are restored to their original shapes by the elasticity after being deformed in a radially outward direction of the cylinder.

11. The intrauterine radiation device of claim 1, wherein the split sleeves are hinged with the cylinder, and are bent at front ends thereof in a radially inward direction.

12. An intrauterine radiation device having individually inflatable balloons, comprising:
   a hollow cylindrical cylinder in which a plurality of air tubes are installed and into which radiation source mobile instruments are inserted and through which the radiation source mobile instruments pass;
   a plurality of front balloons that are mounted on an outer circumferential surface of a front end of the cylinder in a direction in which the cylinder is inserted, and connected with the air tubes so as to be individually inflated;
   a middle balloon that is spaced apart from the front balloons, mounted on the outer circumferential surface of the cylinder, and connected with one of the plurality of air tubes so as to be inflated; and at least one holder having at least one convex or concave shape that is formed on an inner circumferential surface of the cylinder, and configured to hold the radiation source mobile instruments, wherein the front end of the cylinder is partitioned into at least four split sleeves along a circumferential direction of the cylinder, and each front balloon is mounted on each split sleeve, and is allowed to be simultaneously inflated in thickness and insertion directions of the cylinder.

13. The intrauterine radiation device of claim 12, wherein the holder is a convex holder that protrudes from the inner circumferential surface of the cylinder in a radially inward direction and has a semi-circular cross section.

14. The intrauterine radiation device of claim 12, wherein the holder is a concave holder that is recessed from the inner circumferential surface of the cylinder.

15. The intrauterine radiation device of claim 14, wherein, after the radiation source mobile instrument is mounted on the holder, a shield is mounted around the radiation source mobile instrument.

16. The intrauterine radiation device of claim 12, further comprising a thermoluminescence dosimeter that is installed in the cylinder or the front balloon so as to measure a dose of radiation.

17. An intrauterine radiation device comprising:
a hollow cylindrical cylinder in which a plurality of air tubes are installed and into which radiation source mobile instruments are inserted and through which the radiation source mobile instruments pass;
at least one holder having at least one convex or concave shape that is formed on an inner circumferential surface of the cylinder, and configured to hold the radiation source mobile instruments;
a plurality of front balloons that are mounted on an outer circumferential surface of a front end of the cylinder in a direction in which the cylinder is inserted, and that are connected with the air tubes so as to be individually inflated; and
a thermoluminescence dosimeter that is detachably mounted on an outer circumferential surface of the cylinder so as to measure a dose of radiation,
wherein the front end of the cylinder is partitioned into at least four split sleeves along a circumferential direction of the cylinder, and each front balloon is mounted on each split sleeve, and is allowed to be simultaneously inflated in thickness and insertion directions of the cylinder.

18. An intrauterine radiation device comprising:
a hollow cylindrical cylinder in which a plurality of air tubes are installed;
a radiation source mobile instrument that is introduced into the cylinder and passes through the cylinder;
a plurality of front balloons that are mounted on an outer circumferential surface of a front end of the cylinder in a direction in which the cylinder is inserted, and that are connected with the air tubes so as to be individually inflated; and
at least one holder having at least one convex or concave shape which is formed on an inner circumferential surface of the cylinder and on which the radiation source mobile instrument is mounted,
wherein the front end of the cylinder is partitioned into at least four split sleeves along a circumferential direction of the cylinder, and each front balloon is mounted on each split sleeve, and is allowed to be simultaneously inflated in thickness and insertion directions of the cylinder.

19. The intrauterine radiation device of claim 18, wherein, after the radiation source mobile instrument is mounted on the holder, a shield is mounted around the radiation source mobile instrument so as to shield the radiation.

20. An intrauterine radiation system having individually inflatable balloons, comprising:
a hollow cylindrical cylinder in which a plurality of air tubes are installed and into which radiation source mobile instruments are inserted and through which the radiation source mobile instruments pass;
at least one holder having at least one convex or concave shape that is formed on an inner circumferential surface of the cylinder, and configured to hold the radiation source mobile instruments;
a plurality of front balloons that are mounted on an outer circumferential surface of a front end of the cylinder in a direction in which the cylinder is inserted, and that are connected with the air tubes so as to be individually inflated; and
injection means for injecting air or water so as to inflate the front balloons, wherein the front end of the cylinder is partitioned into at least four split sleeves along a circumferential direction of the cylinder, and each front balloon is mounted on each split sleeve, and is allowed to be simultaneously inflated in thickness and insertion directions of the cylinder.

* * * * *

UNITED STATES PATENT AND TRADEMARK OFFICE
CERTIFICATE OF CORRECTION

| | | |
|---|---|---|
| PATENT NO. | : 8,968,170 B2 | Page 1 of 1 |
| APPLICATION NO. | : 13/496853 | |
| DATED | : March 3, 2015 | |
| INVENTOR(S) | : Gim et al. | |

It is certified that error appears in the above-identified patent and that said Letters Patent is hereby corrected as shown below:

Title page

Item (12) delete "Gim", and insert -- Gim et al. --

Item (75) Inventor: Add: Hong Seok Jang as co-inventor

Signed and Sealed this
Fifth Day of January, 2016

Michelle K. Lee
*Director of the United States Patent and Trademark Office*